United States Patent

Bowers

[11] Patent Number: 5,838,155
[45] Date of Patent: Nov. 17, 1998

[54] UNDERGROUND FORMATION PRODUCIBILITY AND WATER CUT FROM NUCLEAR MAGNETIC RESONANCE DATA USING AN ISOLATED PORE

[75] Inventor: Mark C. Bowers, Houston, Tex.

[73] Assignee: Conoco Inc., Ponca City, Okla.

[21] Appl. No.: 739,665

[22] Filed: Oct. 31, 1996

[51] Int. Cl.$^6$ .................................................. G01R 33/20
[52] U.S. Cl. ............................................................. 324/303
[58] Field of Search .................................... 324/300, 303, 324/306, 346

[56] References Cited

PUBLICATIONS

Miller, M. N. et al., "Spin Echo Magnetic Resonance Logging: Porosity and Free Fluid Index Determination" in Transactions of the 65th Annual Technical Conference and Exhibition of the Society of Petroleum Engineers, New Orleans, Louisiana, Sep. 23–26, 1990, SPE Paper 20561, pp. 321–334.

Coates, G. R., et al., "MRIL in Conoco 33–1 An Investigation of a New Magnetic Resonance Imaging Log" in Transactions SPWLA 32nd Annual Logging Symposium, Jun. 16–19, 1991, Paper DD, pp. 1–23.

Fertl, W. H. and Vercellino, W. C., "Predict Water Cut from Well Logs" in Oil and Gas Journal, Jun. 1978.

Kenyon, W. E. et al., "Pore–Size Distribution and NMR in Microporous Cherty Sandstones" in Transactions SPWLA 30th Annual Logging Symposium, Jun. 11–14, 1989, Paper LL., pp. 1–24.

Prammer, M. G., "NMR Pore Size Distributions and Permeability At the Well Site" in Transactions 69th Annual Technical and Exhibition of the Society of Petroleum Engineers, Sep. 25–28, 1994, SPE Paper 28368, pp. 55–64.

Kenyon, W. E., "Nuclear Magnetic Resonance As A Petrophysical Measurement" in Nuclear Geophysics, 1992, vol. 6, No. 2, pp. 153–171.

Straley, C., et al, "NMR in Partially Saturated Rocks: Laboratory Insights on Free Fluid Index and Comparison with Borehole Logs", SPWLA 32nd Annual Logging Symposium, Jun. 16–19, 1991, Paper CC, pp. 1–25..

Akkurt, R., et al., "NMR Logging of Natural Gas Reservoirs", SPWLA 36th Annual Logging Symposium, Jun. 26–29, 1995, Paper N, pp. 1–10.

Straley, C., et. al., "Core Analysis by Low Field NMR", Proceedings 1994 International Symposium of the Society of Core Analysts, Paper 9404, pp. 43–56.

*Primary Examiner*—Sandra L. O'Shea
*Assistant Examiner*—Michael Eisenberg

[57] ABSTRACT

Potential producibility and the proportion of water and oil produced can be predicted for hydrocarbon bearing reservoirs using an isolated pore model and nuclear magnetic resonance data. The model is based on the use of two bulk volume irreducible/free fluid index cut off times, one based on small pores and the other based on large pores with a throat size that will not permit movement of fluids therefrom.

10 Claims, 1 Drawing Sheet

UNDERGROUND FORMATION PRODUCIBILITY AND WATER CUT FROM NUCLEAR MAGNETIC RESONANCE DATA USING AN ISOLATED PORE

FIELD OF INVENTION

The present invention relates to a system to efficiently and accurately predict potential producibility and more particularly the proportion of water and oil produced from hydrocarbon bearing reservoirs from Nuclear Magnetic Resonance (NMR) data.

BACKGROUND

The oil industry has long been interested in the prediction of potential producibility and the proportion of water and oil that will be produced (referred to as water cut) for hydrocarbon reservoirs. Articles published by M. N. Miller et al., entitled "Spin Echo Magnetic Resonance Logging: Porosity and Free Fluid Index Determination" in Transactions of the 65th Annual Technical Conference of the Society of Petroleum Engineers, New Orleans, La., SPE Paper 20561; and Coates et. al., entitled "MRIL in Conoco 33-1 An Investigation of a New Magnetic Resonance Imaging Log" in Transactions SPWLA 32nd Annual Logging Symposium, 1991, Paper DD, illustrated that it was possible to predict potential producibility for a hydrocarbon reservoir using nuclear magnetic resonance (NMR) data. An article published by W. H. Fertl and W. C. Vercellino entitled "Predict Water Cut from Well Logs" in Oil and Gas Journal, June 1978, illustrated that water cut could also be predicted from well logs. The present invention involves combining these works and the development of a new NMR interpretation model so that potential producibility and water cut can be predicted for hydrocarbon reservoirs with isolated pores.

NMR theory and applications are rather simple. Nuclei with an odd number of protons, like hydrogen nuclei, become aligned parallel to a static magnetic field. These aligned nuclei result in a net magnetic moment parallel to the direction of the static magnetic field much like a dipole magnet becomes aligned with the earth's magnetic field. That condition is the lowest energy state of the system. An external force, in the form of a radio frequency pulse at the Larmor frequency, can perturb the system to a higher energy state. The result is that the net magnetic moment is reoriented. The location of the reoriented net magnetic moment is controlled by the length of the radio frequency pulse. After removal of the radio frequency pulse, the nuclei return to the lowest energy state through a process called relaxation. Relaxation process have been described in a book by T. C. Farrar and E. D. Becker entitled "Pulse and Fourier Transform NMR Introduction to Theory and Methods", 1971 Academic Press, New York, page 458; and a book by J. C. Davis entitled "Advanced Physical Chemistry", 1965, The Ronald Press Company, New York, page 577.

Relaxation is governed by molecular dynamics. In liquids the molecular dynamics are controlled by the size and interactions of the molecules. Water and oils will have different relaxation characteristics and different types of crude oil have different relaxation characteristics because of compositional differences.

In porous media saturated with a fluid(s), relaxation is more complex. Molecules near the solid surface can interact with that surface. Interaction with the surfaces enhances the relaxation processes and the relaxation rate is proportional to the surface area-to-volume ratio of the pores. The constant of proportionality, termed the surface relaxivity, describes the relaxation provoking power of the surfaces.

Two time constants are derived from nuclear magnetic resonance measurements. The longitudinal or spin-lattice relaxation time ($T_1$) refers to a rate constant that characterizes the return of the net magnetization parallel to the static magnetic field. The transverse or spin-spin ($T_2$) relaxation time refers to a rate constant that characterizes the decay rate of magnetization in an X-Y plane.

Nuclear magnetic resonance measurements can be made with laboratory spectrometers or well logging sondes. These instruments are designed to detect the change in magnetization as a function of time. That data is then used to derive the relaxation rate constants. For any instrument configuration, the apparatus will only respond to nuclei within a defined volume. Different nuclei can be sensed because each type of nucleus can only be reoriented by a radio frequency pulse with a certain frequency. For hydrogen nuclei, the frequency is 42.5759 MHZ/Tesla.

$T_2$ measurements are the most commonly used NMR measurement in well logging and petrophysical applications as they are less time consuming than $T_1$ measurements and can be made with a moving well logging sonde. A paper by W. E. Kenyon et al., entitled "Pore Size Distributions and NMR in Microporous Cherty Sandstones" in Transactions SPWLA 30th Annual Logging Symposium, Jun. 11–14, 1989, Paper LL, illustrated how nuclear magnetic resonance data could be transformed in volume-to-surface area distributions of pores contained within a porous media. A second paper by M. G. Prammer entitled "NMR Pore Size Distributions and Permeability At the Well Site" in Transactions 69th Annual Technical and Exhibition of the Society of Petroleum Engineers, Sep. 25–28, 1994, Paper 28368 illustrated another method for deriving volume-to-surface area distributions from nuclear magnetic resonance data.

These volume-to-surface area distributions approximate the pore size distribution of a porous media. An NMR pore size distribution can be used to divide the fluid content into fluids that are mobile and fluids that are immobile. These divisions are made using a relaxation time cut off. Often that time cut off is assumed or determined from NMR measurements from samples that have been centrifuged down to an irreducible water saturation. The time at which there is no longer an NMR signal is the bulk volume irreducible (BVI)/free fluid index(FFI) cut off time. That cut off time can then be applied to the other samples.

BVI refers to the porosity associated with fluids that are immobile and have relaxation times less than the BVI/FFI cut off time. FFI refers to the porosity associated with fluids that are mobile and have relaxation times greater than the BVI/FFI cut off time. The segmentation of fluids into BVI and FFI components can be used to predict potential producibility and water cut.

Potential producibility refers to the types of fluids that can be produced from a potential hydrocarbon bearing reservoir. Some reservoirs will produce only water, some will produce hydrocarbons and water while others will produce only hydrocarbons. NMR data can be used to derive the potential producibility of a reservoir. If the bulk volume water (BVW, the product of water saturation and porosity) of the reservoir is less than the porosity and equal to BVI, only hydrocarbons will be produced. If BVW is less than the porosity and greater than BVI, water and hydrocarbons will be produced. If BVW is equal to the porosity and greater than BVI, only water will be produced.

BVI and FFI can also be used to derive the irreducible water saturation ($S_{wi}$). If $S_{wi}$ is known, water cut can be predicted.

SUMMARY OF INVENTION

The method of the present invention provides a means to predict the percentage of water and oil that will be produced from a hydrocarbon bearing formation. The method is based upon an Isolated Pore Model that uses more than one bulk volume irreducible/free fluid index cut off time. In addition to determining the BVI and FFI cut off based on small pores, a second cut off time which accounts for large pores having a small throat size is determined in order to establish a more accurate model of producibility based on the volume of pores associated with the immobile fluids and the volume of pores associated with mobile fluids. These porosities based on the Isolated Pore Model are then used to determine the irreducible water saturation and relative permeability to water and oil and the percentage of hydrocarbons and water that will be produced.

DETAILED DESCRIPTION OF THE PREFERRED EMBODIMENT

Figure 1:
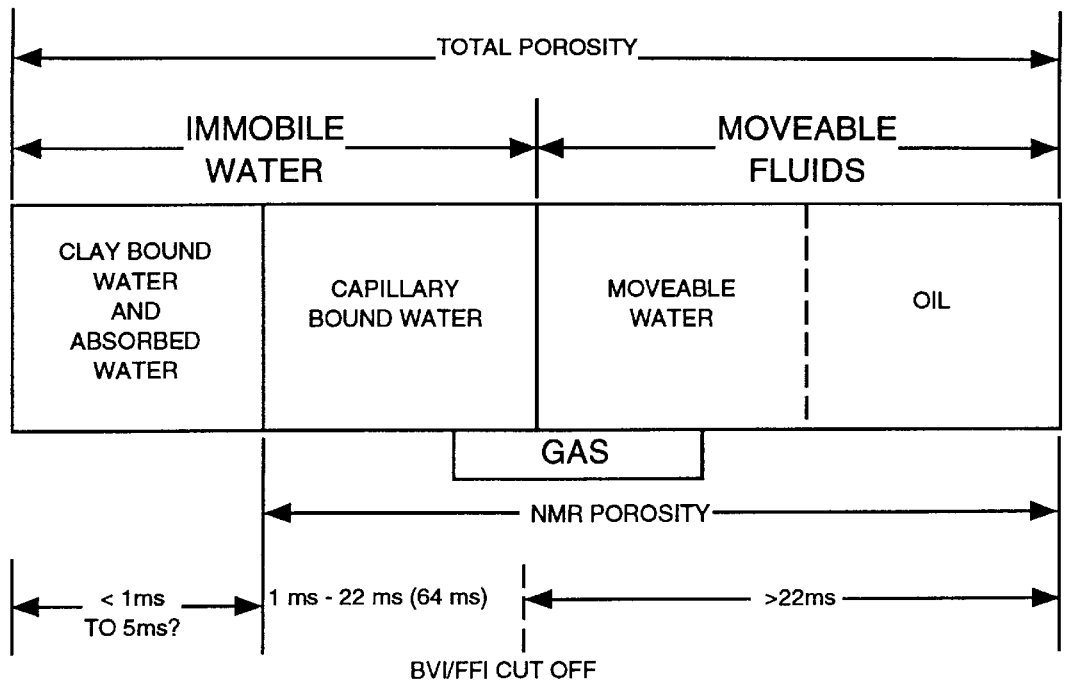
FIG. 1 is an illustration of the basic NMR interpretation model commonly used in the oil industry.

Basic NMR interpretations are based on a relatively simple model. FIG. 1 is an illustration of the basic NMR interpretation model described by Coates et. al., in MRIL in Conoco 33-1: Transaction 32nd Society of Professional Well Log Analysts Annual Logging Symposium, Lafayette, La., 1991, Paper DD. NMR logs measure porosity which can be broken into two components; the Free Fluid Index (FFI) and Bulk Volume Irreducible (BVI). FFI is the amount of porosity associated with fluids that are free to flow and BVI is the amount of porosity associated with fluids that will not flow. Coates et al., (1991) showed that:

$$\phi_{NMR} = BVI + FFI \quad (1)$$

where:
 $\phi$=NMR derived porosity

Potential producibility is a term used to describe the types of fluids likely to be produced from a potential hydrocarbon reservoir. Potential producibility is predicted by comparing BVI to bulk volume water (BVW, the product of water saturation and porosity). The difference between the BVW and BVI is the amount of moveable water in pore volumes. When BVI equals BVW, only hydrocarbons will be produced (if BVW<1). The amount of hydrocarbon present is the difference between $\phi_{NMR}$ and BVW.

Alternatively, potential producibility can be predicted by calculating the irreducible water saturation from NMR data using the equation presented by M. N. Miller et al., entitled "Spin Echo Magnetic Resonance Logging: Porosity and Free Fluid Index Determination" in Transactions of the 65th Annual Technical Conference of the Society of Petroleum Engineers, New Orleans, La., SPE Paper 20561:

$$S_{wi} = 1 - \left( \frac{FFI}{\phi_{NMR}} \right) \quad (2)$$

If $S_{wi}$ equals the water saturation ($S_w$ as determined by traditional log analysis techniques) in a zone, then no water can be produced as it is all immobile. Only hydrocarbons will be produced if $S_w$ is less 1.

FFI and BVI are determined by assuming a BVI/FFI cut off time. That cut off time is often determined with laboratory measurements. A water saturated rock sample from a reservoir is placed in a centrifuge, or on a porous plate apparatus until an irreducible water saturation is achieved. This occurs when fluids are no longer extracted from the sample under certain pressure (centripetal force) conditions. A $T_2$ relaxation curve is measured with an NMR spectrometer and a pore size distribution calculated for the rock sample after irreducible water saturation condition is achieved. The longest $T_2$ time associated with the pore size distribution is the BVI/FFI cut off time.

In a paper entitled "Nuclear Magnetic Resonance As A Petrophysical Measurement" in Nuclear Geophysics, 1992, v.6, n.2 pp. 153–171, Kenyon describes the techniques to the theory behind using centrifuge or porous plate experiments to obtain the BVI/FFI cut off times. In a paper entitled "NMR in Partially Saturated Rocks: Laboratory Insights on Free Fluid Index and Comparison with Borehole Logs" in SPWLA 32nd Annual Logging Symposium, paper CC, pp. 1–25 also described the techniques to estimate the BVI/FFI cut off times.

The largest throat size associated with the pores containing the irreducible fluids can be determined from the pressure used to achieve an irreducible water saturation. That throat size is calculated using the Laplace Equation which has the form:

$$P_c = \frac{2\gamma \cos\theta}{r}$$

where
 $P_c$=capillary pressure
 $\gamma$=interfacial tension of the fluid
 $\theta$=contact angle of the fluid
 r=throat radius Other, less precise, methods can also be used to estimate the BVI/FFI cut off time. An examination of thin sections of rock material and core samples can be used to estimate the approximate BVI/FFI cut off time. The petrographic and petrologic examination is used to identify a subpopulation of pores that are likely to be isolated or associated with small throats. That subpopulation of pores can then be identified in the NMR pore size distributions. The $T_2$ value, which is proportional to the surface area-to-volume ratio or pore size, associated with these pores is the BVI/FFI cut off time.

There are a number of assumptions associated with the basic NMR interpretation model set forth above. First, hydrocarbons always have relaxation times greater than the BVI/FFI cut off time. Second, and just as important, there is an assumption that large pores always have large throats. Therefore, only a single BVI/FFI cut off time is needed. However, it has been recognized that there are many occasions where large pores are associated with small throats and this invention combines this recognition with NMR relaxation data to achieve a more accurate producibility model. These small throats control potential producibility of the rock. In carbonates, large pores (>50 micrometers in diameter) are often isolated or associated with small throats. In sandstones, pores formed by dissolution of grains can also be associated with small throats. When large pores are associated with small throats and the basic (prior art) NMR interpretation model used, the result will be an incorrect prediction of potential producibility because these pores will be seen as FFI pores. Zones that will produce only hydrocarbons will be interpreted to produce large volumes of water. If larger BVI/FFI cut off times are used to account for these pores, zones that will produce water will often be interpreted to produce only hydrocarbons.

Figure 2:
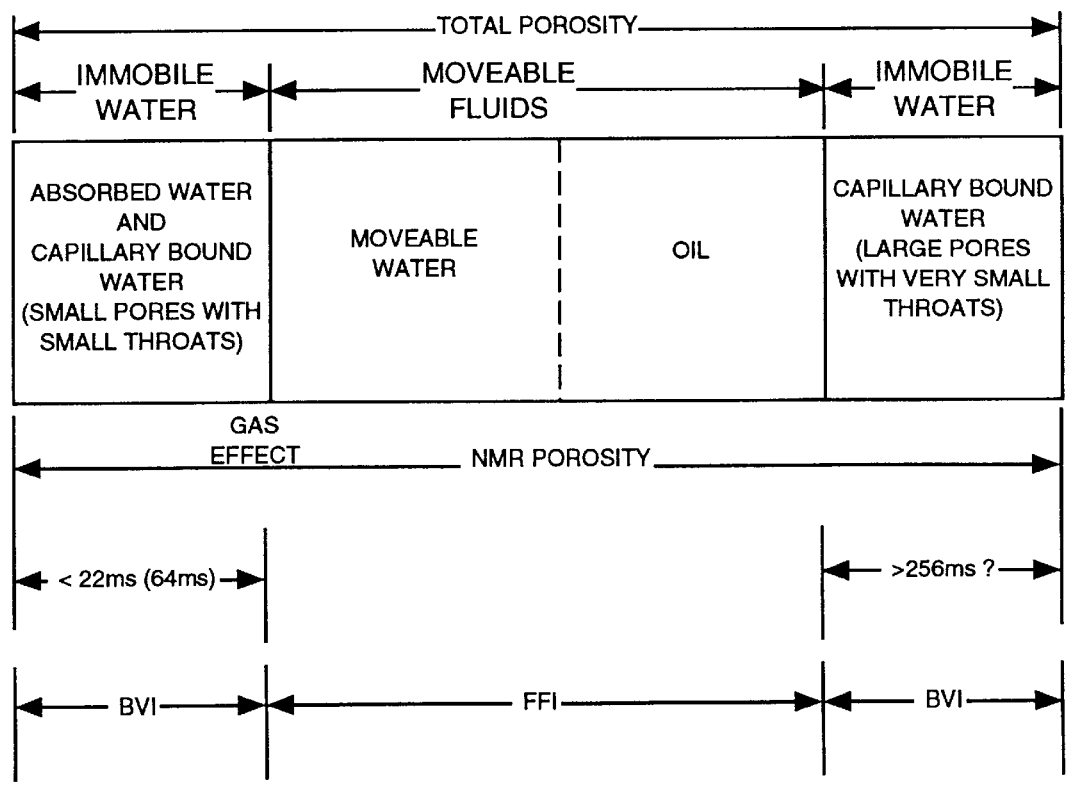
FIG. 2 is an illustration of the isolated pore model of the present invention for predicting potential producibility and volumes of water and oil that will be produced from a hydrocarbon bearing reservoir.

FIG. 2 is an illustration of the Isolated Pore Model (IPM) of the present invention which uses two BVI/FFI cut off times. BVI is calculated using the following:

$$BVI_{IPM} = \phi_s + \phi_L \quad (4)$$

where:

$BVI_{IPM}$=bulk volume irreducible calculated using IPM $\phi_s$=the amount of porosity associated with a $T_2$ relaxation time less than a predetermined value $\phi_L$=the amount of porosity associated with a $T_2$ relaxation time greater than a predetermined value The range of times for $\phi_s$ (small pores with small throats) is generally between 20 and 64 milliseconds. $\phi_s$ times have been used routinely in determining BVI/FFI and development of these values is described in publications such as "NMR Logging of Natural Gas Reservoirs" in SPWLA 36th Annual Logging Symposium, 1995, Paper N. by Akkurt et al., and "Core Analysis by Low Field NMR" in Proceedings 1994 International Symposium of the Society of Core Analysts Paper 9404 by Straley et al., describe that the two most commonly used $\phi_s$ times are 16 and 33 milliseconds. The range of times for $\phi_L$ (large pores with small throats) is generally between 200 and 512 milliseconds. $\phi_L$ times have not been used previously to determine accurate BVI/FFI calculations. This range of values covers typical oil reservoir rocks but there are formations that will have $T_2$ times outside this range, that define large pores with small throats and thus porosity associated with irreducible fluids. In addition to using the NMR measurements of partial saturations to calculate a $T_2$ relaxation curve and consequently $\phi_L$, this throat size/pore size relationship can be derived by other methods including visually analyzing thin sections (a thin slice of core), by examining a core sample in a more gross state, or by image analysis involving digitizing images of porosity in thin sections.

FFI associated with the IPM model is calculated using:

$$FFI_{IPM} = \phi_{NMR} - (\phi_s + \phi_L) \quad (5)$$

where:

$FFI_{IPM}$=free fluid index calculated using IPM $S_{wi}$ can also be calculated from IPM:

$$Swi_{IMP} = 1 - \frac{\phi_{NMR} - (\phi_s + \phi_L)}{\phi_{NMR}} \quad (6)$$

where:

$Swi_{IMP}$=irreducible water saturation using IMP

The IPM model is used to account for large pores associated with small throats. Once $BVI_{IMP}$, $FFI_{IMP}$ and $Swi_{IMP}$ are calculated, they can be used to better predict potential producibility. This contrasts to the prior art practice of predicting producibility from BVI and FFI calculations based only on $T_2$ times less than a predetermined value or functionally on the assumption that large pores have large throats. Previously BVI was based on small pores with small throats. Everything else was FFI including large pores with small throats such as in carbonate reservoirs or small pores with large throats such as in fine grain sandstones. Small pores tend to contain water only and therefore in the old model for the one BVI/FFI cut off time, you would typically predict producing less water instead of the reality of more water (higher water cut and higher FFI). Large pores with small throats are seen in the old model as FFI thus over predicting the amount of water to be produced, whereas in reality these small throat pores should be BVI and thus reduce the amount of producible water.

The present invention therefore provides an Isolated Pore Model that takes into consideration large pores with small throats in predicting two different BVI/FFI cut offs, one for small pores and one for large pores with small throats. The prior art method described above predicted only one cut off as shown in FIG. 1 assuming that small pores have small throats and large pores have large throats. The method of this invention has two cut offs, one based on large pores having small throats, by factoring in $\phi_L$ (Equation 3) based on a time $T_2$ greater than a predetermined value generally between 200 and 512 milliseconds.

As an example of the application of this new methodology, the Steffan 1-35 well in Dickinson County, North Dakota, was drilled into a carbonate mound and an examination of the core taken from that well revealed significant amounts of large isolated, vug sized pores (i.e. very large pores with very small throats). The basic NMR model of FIG. 1 was used to determine producibility which turned out to be inaccurate in that none of the interpretations adequately reflected the production data. The IPM model of the present invention was then used incorporating NMR logs and visual core data, as well as laboratory NMR data that gave significantly more accurate producibility values. For that model, $\phi_s$ was associated with a cut off time of 22 milliseconds and $\phi_L$ associated with a cut off time of 350 milliseconds.

Water cut from oil reservoirs can also be predicted using NMR logs and the IPM model. Fertl and Vercellino (1978) in Fertl, W. H., and Vercellino, W. C. "Predict Water Cut From Well Logs": Oil and Gas Journal, June 1978, presented equations to predict water cut when the water saturation ($S_w$), $S_{wi}$, formation volume factor and water and hydrocarbon viscosities are known. However, for reservoirs with isolated pores, $Sw_{IMP}$ must be used to determine the correct irreducible water saturation. Relative permeability to oil ($K_o$) is predicted using:

$$K_0 = \left( \frac{0.9 - S_w}{0.9 - Swi_{IMP}} \right)^{n_0} \quad (7)$$

where:

$n_o$=an exponent appropriate for the oil phase

Relative permeability to water ($K_w$) is predicted using:

$$K_w = \left( \frac{S_w - Swi_{IMP}}{1 - Swi_{IMP}} \right)^{n_w} \quad (8)$$

where:

$n_w$=an exponent appropriate for the water phase

The water oil ratio (WOR) is then predicted using:

$$WOR = \beta_0 \frac{(\mu_0 K_w)}{(\mu_w K_o)} \quad (9)$$

where:

$\beta_o$=formation volume factor $\mu_o$=viscosity of the oil at formation temperature and pressure $\mu_w$=viscosity of the water at formation temperature and pressure The water cut (WC) is then predicted using:

$$WC = \frac{WOR}{1 + WOR} \quad (10)$$

$Swi_{IMP}$ is obtained from NMR logs and from IPM, while $S_w$ is obtained from a water saturation model using traditional logs and interpretation techniques. The viscosities and formation volume factors must be obtained from other data or be estimated.

Water cut was determined for the Steffan 1-35 well using IPM and water saturation from traditional log analysis techniques. The predicted water cut is the average water cut over the entire perforated interval and assuming that each zone contributes equal flow rates. The predicted water cut was 42% and the actual water cut was 47% and was determined by an extended production test. From the water cut prediction we can interpret that most of the water is being produced out of the lower set of perforations. Potentially, water production could be significantly reduced if the lower set of perforations were squeezed.

By use of the correct NMR interpretation model and the determination of water cut, quantitative predictions of potential producibility are possible. These predictions could have significant economic impact. The application could be used to determine which zones are worth testing and which ones were not, as well as, potentially removing the need for production tests. A more general benefit could be realized as the technology provides information for better reservoir characterization that can be used to optimize reservoir development. The technique is also applicable to the identification of by-passed pay.

Although the present invention has been described in connection with the preferred embodiment, it is not intended to be limited to the specific form set forth here, but on the contrary, it is intended to cover such modifications, alternatives, and equivalents as can be reasonably included in the spirit and scope of the invention by the appended claims.

I claim:

1. A method for determining the porosity of a formation in an underground reservoir where the reservoir rock is determined to have large pores with small throats and where the porosity is associated with the bulk volume irreducible (BVI) and free fluid index (FFI) of the formation comprising;

establishing first and second predetermined values of time $T_2$ taken from a relaxation curve on a reservoir material, which first predetermined value represents the maximum $T_2$ relaxation time for small pores that will not permit the flow of fluids therefrom under expected reservoir conditions and which second predetermined value represents the lowest number for large pores in the material having a small throat size that prevents fluids from migrating from said pores under expected reservoir conditions;

determining the distribution of small pores in the reservoir material based on pore distributions having a $T_2$ relaxation time less than the first predetermined value;

determining the distribution of large pores with small throats in said reservoir material based on pore distributions having a $T_2$ relaxation time greater than the second predetermined value; and summing the small pore distribution and large pore with small throat distributions to determine an accurate BVI/FFI of the formation.

2. The method of claim 1 and further including determining the NMR porosity of the formation using NMR porosity logs and subtracting the accurate BVI to determine the FFI of the formation.

3. The method of claim 1 wherein the second predetermined value of time $T_2$ for determining the distribution of large pore size with small throats in the reservoir material is 200 milliseconds.

4. The method of claim 1 wherein the second predetermined value of time $T_2$ for determining the distribution of large pores with small throats in the reservoir material is in the range of 200 to 512 milliseconds.

5. The method of claim 1 and further including calculating the irreducible water saturation ($S_{wi}$) of the formation material by performing steps to solve the following equation:

$$S_{wi} = 1 - \frac{\phi_{NMR} - (\phi_S + \phi_L)}{\phi_{NMR}}$$

where $\phi_{NMR}$ is the porosity of the reservoir material as measured by NMR porosity logs or NMR spectrometers, where $\phi_s$ is the distribution of reservoir material associated with time $T_2$ less than the first predetermined value, and where $\phi_L$ is the distribution of reservoir material associated with time $T_2$ greater than the second predetermined value.

6. A method for accurately determining the producibility of fluids from a hydrocarbon bearing formation having large pores with small throats in the formation material that will not substantially permit the free flow of fluids therefrom, comprising:

(a) providing $T_2$ relaxation curves derived from NMR measurements of the formation material;

(b) using $T_2$ times less than at least 64 milliseconds to determine the distribution of pores in the formation material that are too small to permit flow of fluids therefrom;

(c) using $T_2$ times greater than at least 200 milliseconds to determine the distribution of large pores that have small throats to prevent the flow of fluids therefrom; and (d) using the determined pore distribution from steps (b) and (c) to calculate the producibility of the formation material.

7. A method for accurately determining the producibility of fluids from a hydrocarbon bearing formation having large pores with small throats in the formation material that will not substantially permit the free flow of fluids therefrom, comprising:

(a) providing $T_2$ relaxation curves derived from NMR measurements of a formation material;

(b) selecting a $T_2$ time for the material that represents the upper limit of small pores that will not allow the free flow of fluids therefrom and to establish a first BVI/FFI cut off time;

(c) selecting a $T_2$ time for the material that represents the lower limit of large pores having throat sizes so small that they will not allow the free flow of fluids from the large pores and to establish a second BVI/FFI cut off time; and (d) using the first and second BVI/FFI cut off times for determining pore distribution of the formation material to accurately evaluate producibility of the formation.

8. The method of claim 7 and further including using the step (b) and step (c) $T_2$ times to determine an accurate total BVI for the formation.

9. The method of claim 8 and further including determining the NMR porosity of the formation using NMR porosity logs or NMR spectrometers and subtracting the accurate total BVI to determine the FFI of the formation.

10. The method of claim 7 wherein the second cut off time is greater than 200 milliseconds.

* * * * *

UNITED STATES PATENT AND TRADEMARK OFFICE
CERTIFICATE OF CORRECTION

PATENT NO. : 5,838,155

DATED : November 17, 1998

INVENTOR(S) :
      Mark C. Bowers

It is certified that error appears in the above-identified patent and that said Letters Patent is hereby corrected as shown below:

Cover Page, the title "Underground Formation Producibility and Water Cut from Nuclear Magnetic Resonance Data Using an Isolated Pore" should be --Underground Formation Producibility and Water Cut from Nuclear Magnetic Resonance Data Using an Isolated Pore Model--.

Column 1, lines 1-4, the title "Underground Formation Producibility and Water Cut from Nuclear Magnetic Resonance Data Using an Isolated Pore" should be --Underground Formation Producibility and Water Cut from Nuclear Magnetic Resonance Data Using an Isolated Pore Model--.

Signed and Sealed this

Sixteenth Day of March, 1999

*Attest:*

Q. TODD DICKINSON

*Attesting Officer*    *Acting Commissioner of Patents and Trademarks*